United States Patent [19]

Rule et al.

[11] Patent Number: 4,968,813

[45] Date of Patent: Nov. 6, 1990

[54] DERIVATIVES OF 4H-THIOPYRAN-1,1-DIOXIDES

[75] Inventors: Norman G. Rule; Teh-Ming Kung, both of Rochester, N.Y.

[73] Assignee: Eastman Kodak Company, Rochester, N.Y.

[21] Appl. No.: 455,656

[22] Filed: Dec. 22, 1989

[51] Int. Cl.$^5$ ............................................ C07D 335/02
[52] U.S. Cl. ...................................................... 549/28
[58] Field of Search .......................................... 549/28

[56] References Cited

U.S. PATENT DOCUMENTS 4,514,481  4/1985  Scozzafava et al. ................... 549/13
4,701,396  10/1987  Hung et al. .......................... 540/141

Primary Examiner—John M. Ford
Assistant Examiner—M. S. Howard
Attorney, Agent, or Firm—David F. Janci

[57] ABSTRACT

Certain new chemical compounds are derivatives of 4H-thiopyran-1,1-dioxides, and are useful as electron-transport agents in electrophotographic elements.

2 Claims, No Drawings

DERIVATIVES OF 4H-THIOPYRAN-1,1-DIOXIDES

FIELD OF THE INVENTION

This invention relates to certain chemical compounds, which are derivatives of 4H-thiopyran 1,1-dioxides. The chemical compounds have unexpectedly good solubility or dispersibility in organic solvents and polymeric binders, and they exhibit good electron-transport properties in electrophotographic elements.

BACKGROUND

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced creation of electron/hole pairs, which are generated by a material (often referred to as a charge-generation material) in the electrophotographic element in response to exposure to the imagewise actinic radiation. Depending upon the polarity of the initially uniform electrostatic potential and the type of materials included in the electrophotographic element, either the holes or the electrons that have been generated migrate toward the charged surface of the element in the exposed areas and thereby cause the imagewise discharge of the initial potential. What remains is a non-uniform potential constituting the electrostatic latent image.

Many electrophotographic elements currently in use are designed to be initially charged with a negative polarity. Such elements contain material which facilitates the migration of positive holes toward the negatively charged surface in imagewise exposed areas in order to cause imagewise discharge. Such material is often referred to as a hole-transport agent. In elements of that type a positively charged toner material is then used to develop the remaining imagewise unexposed portions of the negative polarity potential (i.e., the latent image) into a toner image. Because of the wide use of negatively charging elements, considerable numbers and types of positively charging toners have been fashioned and are available for use in electrographic developers. Conversely, relatively few high quality negatively charging toners are available.

However, for some applications of electro-photography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Thus, positive toner can then be used to develop the exposed surface areas (which will have relatively negative electrostatic potential after exposure and discharge, compared to the unexposed areas, where the initial positive potential will remain).

An electrophotographic element designed to be initially positively charged should, however, contain an adequate electron-transport agent (i.e., a material which adequately facilitates the migration of photo-generated electrons toward the positively charged insulative element surface). Unfortunately (and analogous to the situation with positive and negative toners), many materials having good hole-transport properties have been fashioned for use in electrophotographic elements, but relatively few materials are known to provide good electron-transport properties in electrophotographic elements.

A number of chemical compounds having electron-transport properties are described, for example, in U.S. Pat. Nos. 4,175,960; 4,514,481; 4,474,865; 4,559,287; 4,606,861; and 4,609,602. However, many prior art compounds have one or more drawbacks.

Some prior art electron-transport agents do not perform the electron-transporting function very well, especially under certain conditions or when included in certain types of electrophotographic elements. Also, some cause an undesirably high rate of discharge of the electrophotographic element before it is exposed to actinic radiation (often referred to as high dark decay).

Furthermore, some prior art electron-transport compounds are not soluble or dispersible or have relatively limited solubility or dispersibility in coating solvents of choice or in some polymeric binders desired to be used in charge-transport layers, such that attempts to include sufficient amounts of such electron-transport agents in electrophotographic elements result in some crystallization of the electron-transport agents, which in turn causes problems such as undesirable levels of dark decay and such as unwanted scatter or absorption of actinic radiation intended to pass undisturbed through the charge-transport layer to a radiation-sensitive portion of the element.

Even when sufficient amounts of electron-transport agent for adequate performance can be initially compatibly incorporated in an electrophotographic element, problems can arise thereafter during use of the element. For example, U.S. Pat. No. 4,514,481 describes a number of specific electron-transport agents (e.g., 4 dicyanomethylene-2,6-diphenyl- 4-H-thiopyran-1,1-dioxide) and illustrates incorporating them in polymeric binder layers of electrophotographic elements at a concentration of 30% by weight (based on total weight of the agent and the binder) for good performance. However, in fact, the upper limit of compatibility (solubility or homogeneous dispersibility) of compounds such as 4-dicyanomethylene- 2,6-diphenyl-4-H-thiopyran-1,1-dioxide in many polymeric binders is about 35% by weight. At such concentration the compounds are on the edge of incompatibility. At elevated temperatures, such as the element can encounter during normal use in a copier, the compound can more easily migrate within the binder and tend to form crystalline agglomerates that cause problems such as noted above.

Even if such a problem does not occur, if it is desired to increase the concentration of such an electron-transport agent beyond 35% by weight, there is no leeway to do so. For example, it is well known in the art that increasing the concentration of an electron-transport agent in a polymeric layer, without phase separation, increases the electron-transport mobility of the layer., i.e., photogenerated electrons will move through the layer at a higher velocity and will traverse the layer in a shorter period of time. Such increased mobility enables use of an element, for example, in a high speed copier employing high intensity, short duration imagewise exposure (commonly also referred to as flash exposure), wherein the time it will take for the element to properly discharge, and, thus, the length of the period needed between the end of the exposure step and the beginning of the toner image development step, is determined by the level of electron-mobility within the element. The higher the mobility is, the shorter is the necessary waiting period between exposure and development, and the greater is the number of copies that can be made in a given amount of time.

Thus, there is a continuing need for new chemical compounds that will serve well as electron-transport agents in electrophotographic elements without imparting undesirably high dark decay characteristics thereto and that will also exhibit improved solubility or dispersibility in coating solvents of choice and improved compatibility with polymeric film-forming binders of choice.

The present invention meets this need.

SUMMARY OF THE INVENTION

The present invention provides new chemical compounds, useful as electron-transport agents, which are derivatives of 4H-thiopyran-1,1-dioxides and have the structure

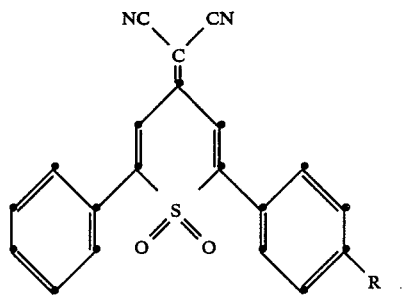

wherein R is alkoxy having 4 to 8 carbon atoms.

The new chemical compounds of the invention useful as electron transPort agents have better solubility or dispersibility in many coating solvents and in many film-forming polymeric binders, that are useful to form one or more layers in electrophotographic elements, than do many previously known electron-transport agents (e.g., those specifically revealed in U.S. Pat. No. 4,514,481). In electrophotographic elements, the inventive chemical compounds can serve as electron-transport agents with good capability of accepting and transporting electrons generated by radiation-activated charge-generation materials in the elements, and they do not impart unacceptably high dark decay properties to the elements. Because of their better solubility in solvents and better compatibility with polymeric binders, the new chemical compounds can be included in electrophotographic elements at concentrations high enough to yield elements that exhibit better electron-transport mobility than they would if the solubility and compatibility of their electron-transport agents were as low as the solubility and compatibility of electron-transport agents such as those revealed in U.S. Pat. No. 4,514,481.

It should be noted that electrophotographic elements, containing electron-transport agents comprising the chemical compounds of this invention, are described and claimed in copending U.S. Patent Application Ser. No. 07/455,665, filed Dec. 22, 1989.

DESCRIPTION OF PREFERRED EMBODIMENTS

The inventive chemical compounds of Structure (I), useful as electron-transport agents in electrophotographic elements, can be prepared from readily available starting materials, for example, by condensation of the appropriate p-R-substituted benzaldehyde (II) with benzalacetone (III), in solution in ethanol/H₂O with the addition of aqueous NaOH, to yield 1-phenyl-5-(4-R-phenyl)-1,4-pentadiene-3-one (IV); (IV) can then be reacted with hydrogen sulfide gas, while in a heated mixture with sodium acetate, dimethylformamide (DMF), and ethanol, to yield 2-phenyl-6-(4-R-phenyl)-2,3,5,6-tetrahydro-4H-thiopyran-4-one (V), which can be reacted with peracetic acid added dropwise to a mixture of (V) and sodium acetate in dichloromethane (DCM), to form the sulfone (VI); (VI) can then be oxidized with dimethylsulfoxide in the presence of small amounts of iodine and H₂SO₄, to yield 2-phenyl-6-(4-R-phenyl)-4H-thiopyran-4-one 1,1-dioxide (VII); (VII) is then converted to 4-dicyanomethylene-2-phenyl-6-(4-R-phenyl)-4H-thiopyran-1,1-dioxide (I) by Knoevenagel condensation with malononitrile in heated ethanol in the presence of piperidine catalyst. This synthetic scheme can be illustrated as follows.

Scheme I

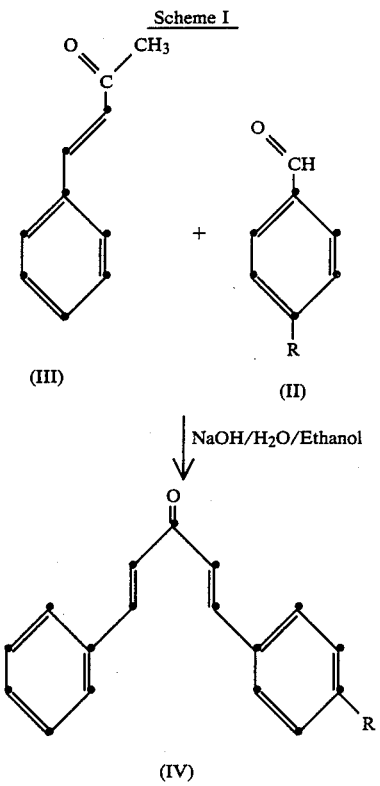

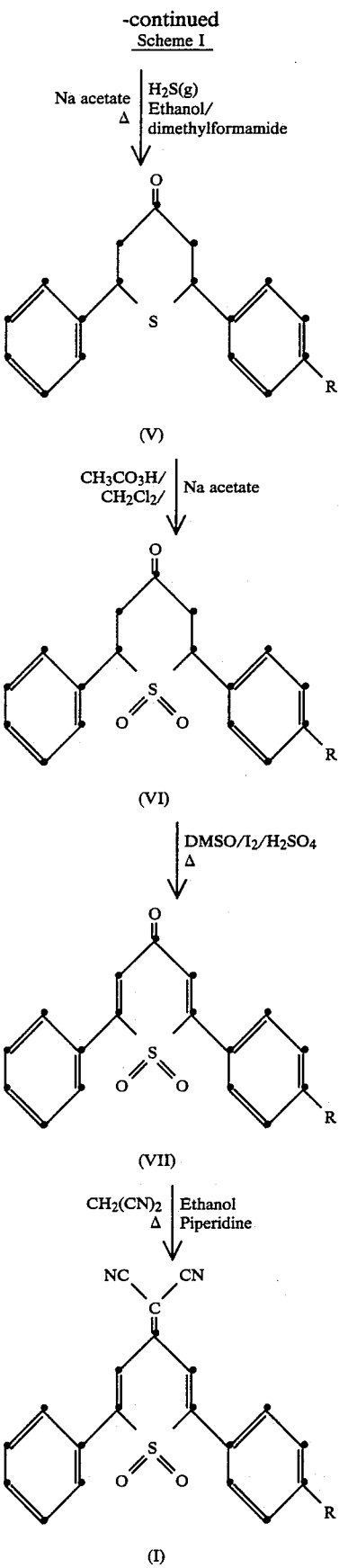

A preferred embodiment of the inventive compounds comprises the Structure (I) compound wherein R is n-butoxy.

To illustrate the solubility/compatibility advantages of Structure (I) compounds, for example, in regard to solubility at room temperature (ca. 22° C.) in dichloromethane (a solvent preferred for use in solvent coating polymeric layers of electrophotographic elements), the preferred Structure (I) compound, 4-dicyanomethylene-2-phenyl-6-(4-n-butoxyphenyl)-4H-thiopyran-1,1-dioxide, has unexpectedly been found to be soluble up to a concentration of at least 6% by weight, and, in regard to compatibility at room temperature with poly[4,4'-(2-norbornylidene)-diphenylene terephthalate-co-azelate] (a preferred film-forming polyester for use in preparing polymeric layers of electrophotographic elements), the same Preferred Structure (I) compound has unexpectedly been found to be compatible therewith up to a concentration of at least 50% by weight. In comparison, the limit of solubility of 4-dicyanomethylene 2,6-diphenyl-4H-thiopyran-1,1-dioxide (Compound 3 of Table I of U.S. Pat. No. 4,514,481, a compound outside the scope of present Structure (I)) in dichloromethane is about 4% by weight, and its limit of compatibility with the polyester identified above is about 35% by weight. Thus, the inventive Structure (I) compound is seen to have significant solubility/compatibility advantages over the prior art compound.

These unexpected advantages are also apparent in comparison to other similar, but previously unknown, compounds just outside the scope of Structure (I). For example the solubility and compatibility limits, in regard to the same solvent and polyester as above, are 2 weight % and 10 15 weight %, respectively, for the compound, 4-dicyanomethylene-2-phenyl-6 -(4-ethoxyphenyl)-4-H-thiopyran-1,1-dioxide, and are about 3.3 weight % and about 20 weight %, respectively, for 4-dicyanomethylene-2-phenyl 6 (4-methoxyphenyl)-4H-thiopyran-1,1-dioxide (both compounds being outside the scope of Structure (I)).

The new chemical compounds of the invention are useful in electrophotographic elements of various types, all of which contain one or more of the chemical compounds of Structure (I) described above to serve as electron-transport agents in the elements. The various types of elements include both those commonly referred to as single layer or single-active-layer elements and those commonly referred to as multiactive, multilayer, or multi active layer elements.

Single-active-layer elements are so named, because they contain only one layer that is active both to generate and to transport charges in response to exposure to actinic radiation. Such elements typically comprise at least an electrically conductive layer in electrical contact with a photoconductive layer. In single-active-layer elements utilizing compounds of the invention, the photoconductive layer contains a charge-generation material to generate electron/hole pairs in response to actinic radiation and an electron-transport material, comprising one or more of the inventive chemical compounds of Structure (I) described above, which is capable of accepting electrons generated by the charge-generation material and transporting them through the layer to effect discharge of the initially uniform electrostatic potential. The photoconductive layer is electrically insulative, except when exposed to actinic radiation, and sometimes contains an electrically insulative polymeric film-forming binder, which may itself be the charge generating material or may be an additional material which is not charge generating. In either case the electron-transport agent is dissolved or dispersed as uniformly as possible in the binder film.

Multiactive elements are so named, because they contain at least two active layers, at least one of which is capable of generating charge (i.e., electron/hole pairs) in response to exposure to actinic radiation and is referred to as a charge-generation layer (hereinafter also referred to as a CGL), and at least one of which is capable of accepting and transporting charges generated by the charge-generation layer and is referred to as a charge-transport layer (hereinafter also referred to as a CTL). Such elements typically comprise at least an electrically conductive layer, a CGL, and a CTL. Either the CGL or the CTL is in electrical contact with both the electrically conductive layer and the remaining CGL or CTL. The CGL contains at least a charge-generation material; the CTL contains at least a charge-transport agent, and either or both layers can contain an electrically insulative film-forming polymeric binder. In multiactive elements utilizing compounds of the invention the charge-transport agent is an electron-transport agent comprising one of the inventive chemical compounds of Structure (I) described above.

Single-active-layer and multiactive electrophotographic elements and their preparation and use, in general, are well known and are described in more detail, for example, in U.S. Pat. Nos. 4,701,396; 4,666,802; 4,578,334; 4,719,163; 4,175,960; 4,514,481; and 3,615,414, the disclosures of which are hereby incorporated herein by reference. The only essential difference of electrophotographic elements utilizing compounds of the present invention from generally known elements is that the new elements contain chemical compounds of Structure (I) as electron-transport agents.

In preparing single-active-layer electrophotographic elements containing compounds of the invention, the components of the photoconductive layer, including any desired addenda, can be dissolved or dispersed together in a liquid and can be coated on an electrically conductive layer or support. The liquid is then allowed or caused to evaporate from the mixture to form the permanent layer containing from about 10 to about 70 percent (by weight) of the inventive electron-transport agent and from about 0.01 to about 50 weight percent of the charge generating material. Included among many useful liquids for this purpose are, for example, aromatic hydrocarbons such as benzene, toluene, xylene and mesitylene; ketones such as acetone and butanone; halogenated hydrocarbons such as dichloromethane, trichloroethane, chloroform, and ethylene chloride; ethers, including ethyl ether and cyclic ethers such as tetrahydrofuran., other solvents such as acetonitrile and dimethylsulfoxide; and mixtures thereof.

In preparing multiactive electrophotographic elements containing compounds of the invention, the components of the CTL can be similarly dissolved or dispersed in such a liquid coating vehicle and can be coated on either an electrically conductive layer or support or on a CGL previously similarly coated or otherwise formed on the conductive layer or support. In the former case a CGL is thereafter coated or otherwise formed (e.g., by vacuum-deposition) on the CTL. The CTL will usually contain from about 10 to about 70 weight percent of the inventive electron-transport agent, although concentrations outside that range may be found to be useful in some cases.

Various electrically conductive layers or supports can be employed in electrophotographic elements containing compounds of the invention, such as, for example, paper (at a relative humidity above 20 percent); aluminum-paper laminates; metal foils such as aluminum foil, zinc foil, etc.; metal plates such as aluminum, copper, zinc, brass and galvanized plates., vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum deposited on transparent film supports in sufficiently thin layers to allow electrophotographic elements prepared therewith to be exposed from either side.

Any charge-generation material can be utilized in elements that contain an electron-transport agent comprising a compound of the invention. Such materials include inorganic and organic (including monomeric organic, metallo-organic and polymeric organic) materials, for example, zinc oxide, lead oxide, selenium, phthalocyanine, perylene, arylamine, polyarylalkane, and polycarbazole materials, among many others.

When solvent-coating a photoconductive layer of a single-active-layer element or a CGL and/or CTL of a multiactive element, a film-forming polymeric binder can be employed. The binder may, if it is electrically insulating, help to provide the element with electrically insulating characteristics. It also is useful in coating the layer, in adhering the layer to an adjacent layer, and when it is a top layer, in providing a smooth, easy to clean, wear-resistant surface.

The optimum ratio of charge-generation or charge-transport material to binder may vary widely depending on the particular materials employed. In general, useful results are obtained when the amount of active charge-generation and/or charge-transport material contained within the layer is within the range of from about 0.01 to about 90 weight percent, based on the dry weight of the layer.

Representative materials which can be employed as binders in charge-generation and charge-transport layers are film-forming polymers having a fairly high dielectric strength and good electrically insulating properties. Such binders include, for example, styrene-butadiene copolymers; vinyl toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers, polyesters, such as poly[ethylene-co-alkylenebis(alkyleneoxyaryl)-phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloacrylates and vinyl acetate such as poly(vinyl m-bromobenzoate-co-vinyl acetate); chlorinated poly(olefins), such as chlorinated poly(ethylene); and polyimides, such as poly[1,1,3-trimethyl-3-(4'-phenyl)-5-indane pyromellitimide].

Binder polymers should provide little or no interference with the generation or transport of charges in the layer. Examples of binder polymers which are especially useful include bisphenol A polycarbonates and polyesters such as poly[4,4'-norbornylidene)diphenylene terephthalate-co-azelate].

CGL's and CTL's can also optionally contain other addenda such as leveling agents, surfactants, plasticizers, sensitizers, contrast-control agents, and release agents, as is well known in the art.

Also, elements containing a compound of the invention can contain any of the optional additional layers known to be useful in electrophotographic elements in general, such as, e.g., subbing layers, overcoat layers, barrier layers, and screening layers.

The following examples are presented to further illustrate the preparation of a specific compound of the invention and its utility as an electron-transport agent in an electrophotographic element.

EXAMPLE 1

Preparation of 4-Dicyanomethylene-2-phenyl-6-(4-n-butoxyphenyl)-4$\underline{H}$-thiopyran-1,1-dioxide (Compound I-A)

Benzalacetone (Compound III of Scheme I, supra) was purchased from Aldrich Chemical Co., U.S.A.

Compound I-A was prepared in accordance with Scheme I, supra. Its structure was confirmed by nuclear magnetic resonance, infrared, and field desorption mass spectrometries.

In the following Example, the structure, preparation, and performance of an electrophotographic element containing a compound within the scope of the present invention are illustrated. Performance is illustrated in regard to electrophotographic sensitivity and dark decay properties.

In illustrating electrophotographic sensitivity in the Example, the element was electrostatically corona-charged to an initial positive potential (about 300 volts) and then exposed to actinic radiation (radiation having peak intensity at a wavelength to which the charge-generation material in the element is sensitive in order to generate electron/hole pairs) in amounts sufficient to photoconductively discharge 50% and 80% of the initial voltage. Electrophotographic sensitivity was measured in terms of the amount of incident actinic radiant energy (expressed in ergs/cm$^2$) needed to discharge the initial voltage down to the desired level. The lower the amount of radiation needed to achieve the desired degree of discharge, the higher is the electrophotographic sensitivity of the element, and vice versa.

In illustrating dark decay properties in the Example, the rate of dissipation of the initial voltage (expressed in V/s, i.e., volts per second) was measured while the element remained in darkness (i.e., before any exposure to actinic radiation). This was accomplished by measuring the initial voltage and the voltage remaining on the element after 2 seconds in darkness and dividing the difference by 2. The lower the rate of discharge in darkness, the better is the dark decay property of the element, i.e., the better is the element's ability to retain its initial potential before exposure.

In the table of performance data in the Example, "Electron transport agent", refers to the chemical compound incorporated in the CTL of an electrophotographic element to serve as an electron-transport agent. "Wt%" refers to the percent by weight of electron-transport agent employed, based on the total weight of polymeric binder and electron-transport agent included in the solution used to coat the CTL of the element.

"$V_o$" refers to the uniform positive potential (in volts) on the element, after it was charged by corona-charging and after any dark decay, such potential having been measured just prior to any exposure of the element to actinic radiation. "DD" refers to the rate of dark decay of the element, prior to exposure to actinic radiation, measured in volts per second (V/s) as described above. "E($V_o$-50%)" refers to the amount of incident actinic radiant energy (expressed in ergs/cm$^2$) that was needed to discharge 50% of $V_o$. "E($V_o$-80%)" refers to the amount of incident actinic radiant energy (expressed in ergs/cm$^2$) that was needed to discharge 80% of $V_o$.

EXAMPLE 2 AND CONTROL A

An electrophotographic element containing an inventive electron-transport agent in its CTL was prepared as follows.

A conductive layer-coated support was prepared by vacuum-depositing a thin conductive layer of aluminum onto a 178 micrometer thickness of poly(ethylene terephthalate) film.

A charge-generation layer (CGL) was prepared by dispersing the charge-generation material, titanyl tetrafluorophthalocyanine (described more extensively in U.S. Pat. No. 4,701,396), in a solution of a polymeric binder, comprising a polyester formed from 4,4'-(2-norbornylidene)diphenol and terephthalic acid:azelaic acid (40:60 molar ratio), in dichloromethane (the weight ratio of charge-generation material:binder being 2:1), ball milling the dispersion for 60 hours, diluting with a mixture of dichloromethane (DCM) and 1,1,2-trichloroethane (TCE) (to yield a final DCM:TCE weight ratio of 80:20) to achieve suitable coating viscosity, coating the dispersion onto the conductive layer, and drying off the solvent to yield a CGL of 0.5 micrometer thickness.

A coating solution for forming a charge-transport layer (CTL) was then prepared comprising 10 weight percent solids dissolved in dichloromethane. The solids comprised the inventive electron-transport agent, Compound I-A, prepared as in Example 1 above and a polymeric binder comprising a polyester formed from 4,4'-(2-norbornylidene)diphenol and terephthalic acid:azelaic acid (40:60 molar ratio). The concentration of electron-transport agent was as noted in Table I. The solution was then coated onto the CGL and dried to form the CTL on the CGL. The combined thickness of CGL and CTL was in the range of 7 to 10 micrometers.

The CTL for Control A was prepared and coated in the same manner, except that the electron-transport agent comprised 4-dicyanomethylene-2,6-diphenyl-4$\underline{H}$-thiopyran-1,1-dioxide (Compound 3 of Table I of U.S. Patent 4,514,481, a compound outside the scope of present Structure (I)).

Each of the resultant electrophotographic elements was then corona-charged to a uniform positive potential.

Dark decay rate of the initial potential was measured for each element.

Each of the uniformly charged elements was subjected to simulated imaging exposure by exposing it through the outer surface of the CTL to radiation having a wavelength of about 820 nanometers (nm) (to which the charge-generation material is sensitive, in order to generate electron/hole pairs in the CGL) at a rate of about 3 ergs of radiant energy per square centimeter of element surface per second (about 3 ergs/cm$^2$s), and E($V_o$-50%) and E($V_o$-80%) were measured for each element.

Results are presented in Table I.

TABLE I

| Example | Electron-transport agent | Wt. % | $V_o$ (V) | DD (V/s) | $E(V_o\text{-}50\%)$ (ergs/cm$^2$) | $E(V_o\text{-}80\%)$ (ergs/cm$^2$) |
|---|---|---|---|---|---|---|
| Control A | 4-dicyanomethylene-2,6-diphenyl-4H-thiopyran-1,1-dioxide | 30 | 300 | 3 | 4.6 | 12.0 |
| 2 | 4-dicyanomethylene-2-phenyl-6-(4-n-butoxyphenyl)-4H-thiopyran-1,1-dioxide | 50 | 294 | 3 | 5.4 | 14.5 |

The data in Table I show that an electrophotographic element containing a new electron-transport agent of the invention, exhibits similar dark decay properties and electrophotographic sensitivity, compared to an element containing a known electron-transport agent. The data also shows that a Structure (I) compound can be coated at a relatively high concentration in the coating solution (e.g., 5 weight %) to yield a relatively high, yet still compatible, concentration in the CTL binder polymer (e.g., 50 weight %).

The invention has been described in detail with particular reference to certain preferred embodiments thereof, but it should be appreciated that variations and modifications can be effected within the spirit and scope of the invention.

What is claimed is:

1. A chemical compound having the structure

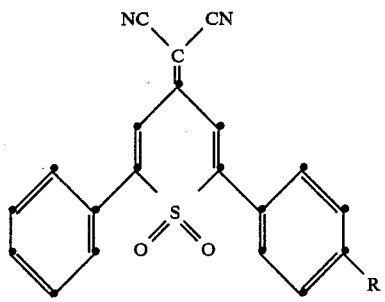

wherein R is alkoxy having 4 to 8 carbon atoms.

2. The chemical compound of claim 1, wherein R is n-butoxy.

* * * * *